United States Patent
Oda

(10) Patent No.: US 8,470,248 B2
(45) Date of Patent: Jun. 25, 2013

(54) GAS IDENTIFYING APPARATUS, GAS IDENTIFYING METHOD GAS HANDLING ASSISTING SYSTEM AND GAS HANDLING ASSISTING METHOD FOR IDENTIFYING GAS BASED ON COLOR OF REACTION SURFACE PRODUCED BY CHEMICAL REACTION

(75) Inventor: Naoki Oda, Tokyo (JP)

(73) Assignee: NEC Corporation, Tokyo (JP)

( * ) Notice: Subject to any disclaimer, the term of this patent is extended or adjusted under 35 U.S.C. 154(b) by 1365 days.

(21) Appl. No.: 11/480,843

(22) Filed: Jul. 6, 2006

(65) Prior Publication Data

US 2007/0009388 A1  Jan. 11, 2007

(30) Foreign Application Priority Data

Jul. 8, 2005  (JP) .................................. 2005-200346

(51) Int. Cl.
*G01N 33/00* (2006.01)
(52) U.S. Cl.
USPC ............. 422/86; 356/402; 356/408; 356/425; 422/87; 422/89; 422/91; 436/167; 436/169; 436/171; 702/22; 702/24
(58) Field of Classification Search
USPC ................ 356/402, 408, 425; 422/86, 87, 89, 422/91; 436/167, 169, 171; 702/24, 22
See application file for complete search history.

(56) References Cited

U.S. PATENT DOCUMENTS

| | | | |
|---|---|---|---|
| 6,228,657 B1 | 5/2001 | Genovese et al. | |
| 6,278,521 B1* | 8/2001 | Jablonski et al. | 356/402 |
| 6,295,506 B1* | 9/2001 | Heinonen et al. | 702/104 |
| 6,579,231 B1* | 6/2003 | Phipps | 600/300 |
| 7,005,982 B1* | 2/2006 | Frank | 340/539.26 |
| 2002/0197735 A1* | 12/2002 | Amirkhanian | 436/517 |
| 2002/0197736 A1* | 12/2002 | Amirkhanian | 436/517 |
| 2006/0008919 A1* | 1/2006 | Boay et al. | 436/164 |
| 2006/0290927 A1* | 12/2006 | Patel et al. | 356/319 |

FOREIGN PATENT DOCUMENTS

| | | |
|---|---|---|
| JP | 2001-343328 | 12/2001 |
| JP | 2003-503715 | 1/2003 |

OTHER PUBLICATIONS

Japanese Office Action dated Dec. 15, 2010 with a partial English translation.

* cited by examiner

*Primary Examiner* — Brian R Gordon
*Assistant Examiner* — Shogo Sasaki
(74) *Attorney, Agent, or Firm* — McGinn IP Law Group, PLLC

(57) ABSTRACT

A detector detects the color of a medium after a gas to be identified and a reagent have chemically reacted with each other on the medium. A controller identifies color information, which is most similar to the color detected by the detector, from color information stored in a spectral database, and reads gas identifying information related to the identified color information, as gas identifying information representing the gas to be identified, from the spectral database.

16 Claims, 12 Drawing Sheets

Fig. 4

1c SPECTRAL DATABASE

| REAGENT NAMES | GAS IDENTIFYING INFORMATION | COLOR CHANGE INFORMATION (SPECTRAL INFORMATION) ||
|---|---|---|---|
| | | λ | STRENGTH |
| A | a | 1 | aaa |
| | | 2 | bbb |
| | | 3 | ccc |
| | | ⋮ | ⋮ |
| | | 256 | nnn |
| B | b | 1 | aba |
| | | 2 | cdc |
| | | ⋮ | ⋮ |
| | | 256 | aaa |
| C | c | 1 | bbb |
| | | 2 | ddd |
| | | ⋮ | |
| | | 256 | eee |

1c1  1c2  1c3 COLOR INFORMATION

Fig. 5

1d1b MEMORY

| λ | DETECTED VALUE | | | | Sb(∧) | ∧ (BAND VALUE) |
|---|---|---|---|---|---|---|
| | S0 | S1 | SX | S | | |
| 1 | | | | | | |
| 2 | | | | | | |
| 3 | | | | | | |
| 4 | | | | | | |
| ⋮ | | | | | ⋮ | |
| 256 | | | | | | 64 |

Binning = 4

Fig. 6

2b HANDLING INFORMATION STORAGE UNIT

| GAS IDENTIFYING INFORMATION (2b1) | HANDLING INFORMATION (2b2) |
|---|---|
| a | ××× |
| b | ×○○ |
| c | △△△ |

Fig. 7

2c HANDLING CENTER STORAGE UNIT

| HANDLING CENTER INFORMATION (2c1) | TERRITORY (2c2) |
|---|---|
| ○○○○○ | AA |
| △△△○ | BB |
| ××○○ | DD |

GAS IDENTIFYING APPARATUS, GAS
IDENTIFYING METHOD GAS HANDLING
ASSISTING SYSTEM AND GAS HANDLING
ASSISTING METHOD FOR IDENTIFYING
GAS BASED ON COLOR OF REACTION
SURFACE PRODUCED BY CHEMICAL
REACTION

BACKGROUND OF THE INVENTION

1. Field of the Invention

The present invention relates to a gas identifying apparatus, a gas identifying method, a gas handling assisting system and a gas handling assisting method, and more particularly to a gas identifying apparatus, a gas identifying method, a gas handling assisting system and a gas handling assisting method for identifying a hazardous gas, for example.

2. Description of the Related Art

Heretofore, there has been known a gas detecting device for changing the color of a reagent based on a chemical reaction between a gas such as a hazardous gas or the like and the reagent. For example, U.S. Pat. No. 6,228,657B1 refers to an M256 chemical agent detection kit.

The gas detecting device comprises a reagent, an ampule containing the reagent, and a medium such as paper. When the ampule is broken, the reagent in the broken ampule flows into the medium. When the reagent flows into the medium, the reagent chemically reacts with a gas that is held in contact with the medium. The chemical reaction changes the color of the reagent, and the change in the color of the reagent changes the color of the medium. The user recognizes the intensity of the gas in accordance with the change in the color of the medium.

The gas detecting device suffers the following problems:

The operation of the gas detecting device is not easy. It is time-consuming to operate the gas detecting device, and the gas detecting device needs to be operated by two persons. The gas detecting device lacks an ability to control environmental elements such as temperature, ultraviolet radiation, etc. The reproducibility and reliability of chemical reactions that are developed by the gas detecting device are poor. The user judges the color of the medium (reagent), and the judgment that is made by the user is nonobjective.

U.S. Pat. No. 6,228,657B1 discloses a reader that is designed to make up for the shortcomings of the gas detecting device.

Specifically, the disclosed reader has automatized the operation of the gas detecting device. As a result, the operating time of the gas detecting device has greatly been reduced.

The reader controls the environmental elements to increase the reproducibility and reliability of chemical reactions.

The reader has a photodiode that is sensitive to at least three wavelength ranges and generates a signal depending on the color of the medium (reagent). Therefore, the user can objectively judge the color of the medium (reagent) based on the generated signal from the photodiode.

The color of the reagent may slightly change depending on the type of the gas to be detected. However, the reader disclosed in U.S. Pat. No. 6,228,657B1 is unable to recognize such a slight change in the color of the reagent. Therefore, the user cannot identify a gas with the reader disclosed in U.S. Pat. No. 6,228,657B1.

SUMMARY OF THE INVENTION

It is an object of the present invention to provide a gas identifying apparatus, a gas identifying method, a gas handling assisting system, and a gas handling assisting method which are capable of identifying a gas in accordance with the color of a reagent which has changed due to a chemical reaction between the reagent and the gas.

To achieve the above object, a gas identifying apparatus according to the present invention identifies a gas to be identified in accordance with the color of a reagent which has chemically reacted with the gas in a gas detecting device. The gas identifying apparatus comprises a database, a detector, and a controller.

The database stores, in advance, gas identifying information for identifying a gas, and color information as to a color of a reagent which has chemically reacted with the gas identified by the gas identifying information, in relation to each other.

The detector detects the color of the reagent which has chemically reacted with the gas to be identified in the gas detecting device.

The controller identifies color information, which is most similar to the color detected by the detector, from the color information in the database, and reads the gas identifying information, which is related to the identified color information, from the database.

With the above arrangement, color information, which is most similar to the color of the reagent which has chemically reacted with the gas to be identified, is identified from the color information stored in the database, and the gas identifying information related to the identified color information is read from the database.

Therefore, if gas identifying information and color information related to the gas to be identified are stored in the database, then the gas can be identified with high accuracy without the need for a decision by the user. Even if the color of the reagent changes slightly, it is possible to identify the gas. It is thus possible to identify the gas in accordance with the color of reagent which has changed by the chemical reaction with the gas.

The gas identifying apparatus should preferably be arranged as follows:

The reagent chemically reacts with the gas to be identified when the reagent flows into a medium that is held in contact with the gas to be identified in the gas detecting device.

The database stores, as the color information, color change information that represents a change from the color of the medium before the reagent flows into the medium to the color of the medium after the reagent flows into the medium and chemically reacts with the gas.

The detector detects the color of the medium before the reagent flows into the medium and the color of the medium after the reagent flows into the medium and chemically reacts with the gas.

The controller comprises a color change detector and a gas identifier.

The color change detector detects the change in the color of the medium in accordance with detected results from the detector.

The gas identifier identifies color change information, which is most similar to the change in the color of the medium which is detected by the color change detector, from the color change information in the database, and reads the gas identifying information related to the identified color change information from the database.

With the above arrangement, a gas to be identified is identified in accordance with a change in the color of the medium. The change in the color of the medium represents the type of the gas that has chemically reacted with the reagent. Therefore, the gas to be identified can be identified highly accurately.

Furthermore, the gas identifying apparatus should preferably be arranged as follows:

The database stores, as the color change information, spectral information that represents a spectrum indicative of the change in the color of the medium.

The detector detects the spectrum of the color of the medium before the reagent flows into the medium and the spectrum of the color of the medium after the reagent flows into the medium and chemically reacts with the gas.

The color change detector detects a spectrum which indicates the change in the color of the medium in accordance with detected results from the detector.

The gas identifier identifies spectral information, which represents a spectrum that is most similar to the spectrum representing the change in the color of the medium that is detected by the color change detector, from the spectral information in the database, and reads the gas identifying information related to the identified spectral information from the database.

With the above arrangement, a change in the color of the medium is identified by a spectrum. Therefore, the gas to be identified can be identified highly accurately.

Preferably, the gas identifier identifies spectral information, which represents a spectral waveform which is most similar to the waveform of the spectrum representing the change in the color of medium which is detected by the color change detector, and which also represents a spectral waveform whose degree of conformity with the waveform of the spectrum representing the change in the color of the medium is of a predetermined value or greater, from the spectral information in the database, and reads the gas identifying information related to the identified spectral information from the database.

With the above arrangement, the gas to be identified can be identified highly accurately.

Furthermore, the gas identifying apparatus should preferably be arranged as follows:

The database stores the gas identifying information and an absorption line obtained from the color of the reagent which has chemically reacted with the gas identified by the gas identifying information, in relation to each other.

The controller identifies an absorption line in accordance with the color detected by the detector, identifies an absorption line, which is most similar to the identified absorption line, from the absorption line in the database, and reads the gas identifying information, which is related to the absorption line which is identified from the absorption line in the database, from the database.

With the above arrangement, it is possible to identify a gas to be identified in accordance with the absorption line of a material which is produced due to the chemical reaction between the gas and the reagent.

Preferably, the database stores color information depending on a detected result from the detector when the detector detects the color of the reagent which has chemically reacted with the gas identified by the gas identifying information.

With the above arrangement, the color information that is stored in the database depends on the characteristics of the detector. Therefore, it is possible to easily match the color information in the database and the detected result from the detector.

The detector should preferably comprise a light-emitting element for applying light to the medium, a photodetector, and a light guide for guiding the light, which is applied from the light-emitting element and then reflected from the medium, to the photodetector.

With the above arrangement, the light guide guides the light, which is applied from the light-emitting element and then reflected from the medium, to the photodetector. The photodetector can thus reliably detect the reflected light.

The gas identifying apparatus should preferably be arranged as follows:

The light guide comprises an elliptical mirror, and the detector comprises an emitted-light guiding optical fiber for guiding the light, which is applied from the light-emitting element, to the medium, and a reflected-light guiding optical fiber for guiding the light, which is reflected from the medium, to a focal position of the elliptical mirror, the photodetector is disposed at another focal position of the elliptical mirror.

With the above arrangement, the light applied from the light-emitting element is guided through the emitted-light guiding optical fiber to the medium, and the light reflected from the medium is guided through the reflected-light guiding optical fiber to the elliptical mirror. Therefore, the detector and the gas detecting device including the reagent can be connected to each other by the optical fibers. Consequently, the gas detecting device and the detector can be spaced from each other.

Since the elliptical mirror guides the reflected light, which is guided by the reflected-light guiding optical fiber, to the photodetector, even if the direction along which the reflected light guided by the reflected-light guiding optical fiber may not be constant due to a flexing of the reflected-light guiding optical fiber, the photodetector is capable of reliably receiving and detecting the reflected light.

The gas identifying apparatus should preferably be arranged as follows:

The light guide comprises an elliptical mirror and a slit, which is disposed at a focal position of the elliptical mirror, for passing therethrough the light reflected from the medium. The detector is disposed at another focal position of the elliptical mirror.

With the above arrangement, the photodetector is capable of reliably detecting the light which is applied from the light-emitting element and then reflected from the medium.

The gas identifying apparatus should preferably further comprise a transmitter for sending the gas identifying information that is read by the controller to an external information center.

With the above arrangement, the information of the identified gas can automatically be sent to the external information center.

The gas identifying apparatus should preferably be arranged as follows:

The gas identifying apparatus further comprises a position output unit for generating positional information representing the present position of the gas identifying apparatus. The transmitter sends the positional information generated by the position output unit, together with the gas identifying information, to the external information center.

With the above arrangement, the external information center can automatically be notified of the location where the identified gas is present.

A gas handling assisting system according to the present invention comprises said gas identifying apparatus and an information center for communicating with the gas identifying apparatus. The gas identifying apparatus includes a transmitter for sending gas identifying information to the information center. The information center comprises a communication unit for receiving information sent from the transmitter, and a display unit for displaying the information received by the communication unit.

With the above arrangement, the information center displays the gas identifying information and the positional information sent from the gas identifying apparatus. Therefore, the information center is able to let the user of the information center know the occurrence of the gas, or the occurrence of the gas and the location where the gas is occurring.

Preferably, the information center further comprises a handling information storage unit and a center controller. The handling information storage unit stores the gas identifying information and handling information representing how to handle the gas that is identified by the gas identifying information, in relation to each other. The center controller reads handling information, which is related to gas identifying information received by the communication unit, from the handling information storage unit, and displays the read handling information on the display unit.

With the above arrangement, the user of the information center can be notified of details of how to handle the gas that is occurring.

The gas handling assisting system should preferably be arranged as follows:

The information center further comprises a handling center storage unit for storing handling center information representing a handling center and a territory covered by the handling center, in relation to each other.

The center controller identifies a handling center whose territory includes a position represented by positional information received by the communication unit, by referring to the handling center storage unit, and controls the communication unit to send the positional information and the read handling information to the identified handling center.

With the above arrangement, the handling center, whose territory covers the location where the gas is occurring, can be notified of the location where the gas is occurring and the details of how to handle the occurring gas.

The above and other objects, features, and advantages of the present invention will become apparent from the following description with reference to the accompanying drawings which illustrate examples of the present invention.

BRIEF DESCRIPTION OF THE DRAWINGS

FIG. 4 is a diagram showing details of a spectral database;

FIG. 5 is a diagram showing details of a memory;

FIG. 6 is a diagram showing details of a handling information storage unit;

FIG. 7 is a diagram showing details of a handling center storage unit;

DETAILED DESCRIPTION OF THE PREFERRED EMBODIMENTS

Figure 1:
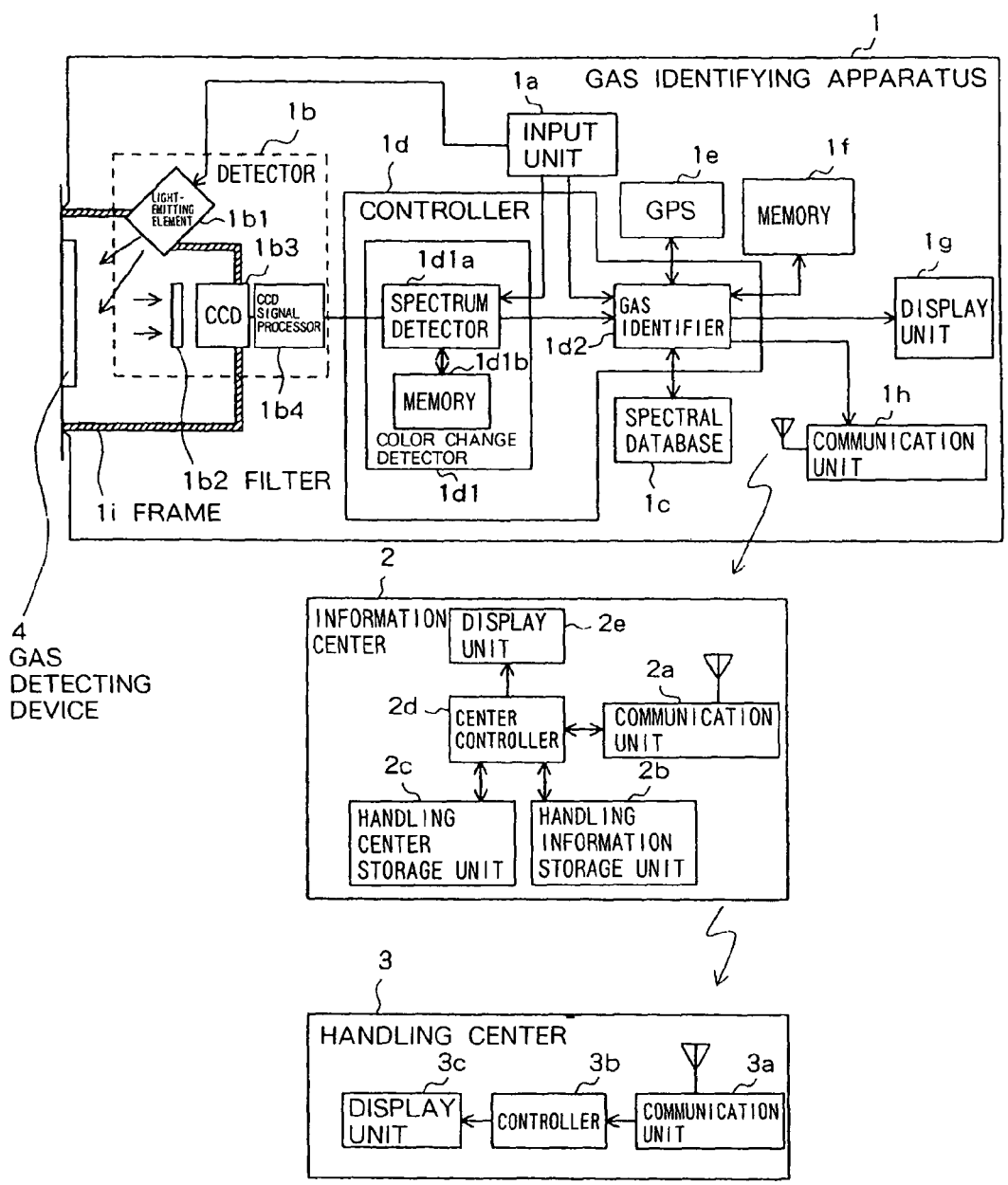
FIG. 1 is a block diagram of a gas handling assisting system according to a first embodiment of the present invention.

FIG. 1 shows a gas handling assisting system according to a first embodiment of the present invention in block form.

As shown in FIG. 1, the gas handling assisting system comprises gas identifying apparatus 1, information center 2, and handling center 3.

Gas identifying apparatus 1 comprises input unit 1a, detector 1b, spectral database (hereinafter referred to as "DB") 1c, controller 1d, GPS 1e, memory 1f, display unit 1g, communication unit 1h, and frame 1i. Detector 1b comprises light-emitting element 1b1, filter 1b2, CCD 1b3, and CCD signal processor (hereinafter referred to as "processor") 1b4 including an ADC (Analog-to-Digital Converter). Controller 1d comprises color change detector 1d1 and gas identifier 1d2. Color change detector 1d1 comprises spectrum detector 1d1a and memory 1d1b.

Information center 2 comprises communication unit 2a, handling information storage unit 2b, handling center storage unit 2c, center controller 2d, and display unit 2e.

Handling center 3 comprises communication unit 3a, controller 3b, and display unit 3c.

Gas identifying apparatus 1 can hold at least mediums 43 of gas detecting device 4 in frame 1i.

Figure 2:
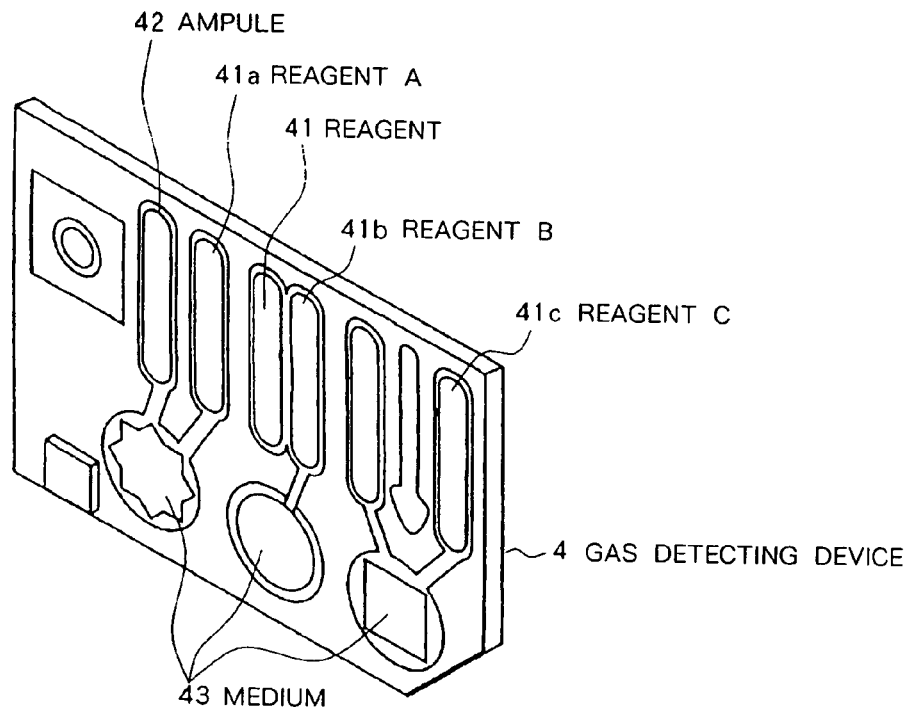
FIG. 2 is a perspective view of a gas detecting device.

FIG. 2 shows an example of gas detecting device 4 in perspective view.

As shown in FIG. 2, gas detecting device 4 has reagents 41, ampules 42 containing respective reagents 41, and mediums 43 such as of paper. When each of ampules 42 is broken, reagent 41 in broken ampule 42 flows into corresponding medium 43.

Specifically, gas detecting device 4 has a plurality of ampules 42 containing respective reagents 41 which are different from each other. In the present embodiment, gas detecting device 4 has reagent 41a entitled "A", reagent 41b entitled "B", and reagent 41c entitled "C".

When reagent 41 flows into corresponding medium 43, reagent 41 chemically reacts with a gas (e.g., a gas to be identified) that is held in contact with medium 43. Reagent 41 and medium 43 change their colors due to the chemical reaction between reagent 41 and the gas. Gas detecting device 4 may be the M256 kit disclosed in U.S. Pat. No. 6,228,657B1, for example.

Referring back to in FIG. 1, gas identifying apparatus 1 identifies the gas in accordance with the color of reagent 41 that has chemically reacted with the gas in gas detecting device 4. Specifically, gas identifying apparatus 1 identifies the gas in accordance with the color of medium 43 which contains reagent 41 that has chemically reacted with the gas to be identified.

Input unit 1a comprises operating switches, and receives inputs from the user, e.g., a dark-current measuring instruction, a light-emitting instruction, and a binning instruction.

When input unit 1a receives a dark-current measuring instruction, input unit 1a supplies the dark-current measuring instruction to controller 1d, or specifically spectrum detector 1d1a. When input unit 1a receives a light-emitting instruction, input unit 1a supplies the light-emitting instruction to detector 1b, or specifically light-emitting element 1b1, and controller 1d, or specifically spectrum detector 1d1a. When input unit 1a receives a binning instruction, input unit 1a supplies the binning instruction to controller 1d, or specifically spectrum detector 1d1a and gas identifier 1d2. Alternatively, a predetermined binning instruction may be set in controller 1d.

Detector 1b detects the color of reagent 41 that has chemically reacted with the gas to be identified. Specifically, detector 1b identifies the color of medium 43 which contains reagent 41 that has chemically reacted with the gas to be identified.

In the present embodiment, detector 1b detects the color of medium 43 before reagent 41 flows into medium 43 and the color of medium 43 after reagent 41 flows into medium 43 and chemically reacts with the gas to be identified. Specifically, detector 1b detects the spectrum of the color of medium 43 before reagent 41 flows into medium 43 and the spectrum of the color of medium 43 after reagent 41 flows into medium 43 and chemically reacts with the gas to be identified.

When light-emitting element 1b1 receives a light-emitting instruction from input unit 1a, light-emitting element 1b1 emits and applies light to medium 43. Light-emitting element 1b1 should preferably, but not necessarily, comprise a halogen lamp or an incandescent lamp, for example.

Medium 43 reflects the light applied from light-emitting element 1b1. When medium 43 contains reagent 41 that has chemically reacted with the gas to be identified, the light reflected by medium 43 represents the color of reagent 41 that has chemically reacted with the gas to be identified.

Frame 1i prevents any light, which is different from the light applied from light-emitting element 1b1, from being applied to gas detecting device 4.

Filter 1b2 comprises a linear variable filter.

Figure 3:
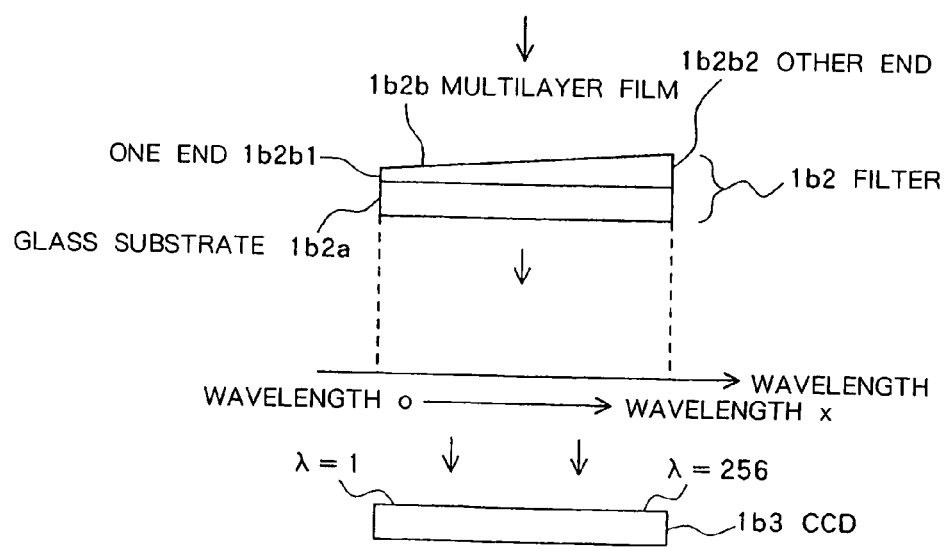
FIG. 3 is a schematic view of a filter.

FIG. 3 schematically shows an example of filter 1b2. Those parts in FIG. 3 which are identical to those shown FIG. 1 are denoted by identical reference characters in FIG. 3.

As shown in FIG. 3, filter 1b2 comprises glass substrate 1b2a and multilayer film 1b2b that is disposed on glass substrate 1b2a. Multilayer film 1b2b has its thickness progressively greater from one end 1b2b1 to other end 1b2b2. Therefore, the wavelength of light that passes through filter 1b2 gradually changes from one end 1b2b1 to other end 1b2b2 (see FIG. 3).

In the present embodiment, the light of wavelength from 380 to 720 nm passes through filter 1b2. The wavelength range that passes through filter 1b2 should not be limited from 380 to 720 nm but can be changed as appropriate.

Referring back to FIG. 1, CCD 1b3 detects light that has passed through filter 1b2. In the present embodiment, CCD 1b3 has 256 photodetectors λ. Each of photodetectors λ (λ=1, 2, . . . , 256) detects light that has passed through filter 1b2. Therefore, each of photodetectors λ detects light of a different wavelength.

CCD 1b3 generates a signal depending on the intensity of light detected by each of photodetectors λ. For example, CCD 1b3 generates the spectrum of the color of reagent 41 that has chemically reacted with the gas to be identified, or in other words, the spectrum of the color of medium 43 that contains reagent 41 that has chemically reacted with the gas to be identified. CCD 1b3 and filter 1b2 jointly make up a light receiving unit.

Processor 1b4 converts the output signal from CCD 1b3 into a digital value.

DB 1c stores, in advance, gas identifying information for identifying gases and color information as to the color of reagents that have chemically reacted with gases identifiable by the gas identifying information, in relation to each other.

For example, DB 1c stores color change information as the color information. The color change information represents a change from the color of medium 43 before reagent 41 flows into medium 43 to the color of medium 43 after reagent 41 chemically reacts with the gas. In the present embodiment, DB 1c stores spectral information as the color change information. The spectral information represents a spectrum indicating a change in the color of medium 43 due to the chemical reaction between a gas to be identified by the gas identifying information and reagent 41.

In the present embodiment, DB 1c stores color information depending on a detected result from detector 1b when detector 1b detects the color of reagent 41 (medium 43) which has chemically reacted with a gas to be identified by the gas identifying information.

FIG. 4 shows an example of DB 1c.

As shown in FIG. 4, DB 1c stores reagent names 1c1, gas identifying information 1c2, and color information 1c3 in relation to each other.

In DB 1c shown in FIG. 4, for example, reagent "A", gas identifying information "a", and the spectrum of the color of reagent "A" which has chemically reacted with a gas identified by gas identifying information "a", or specifically a change in the color of medium 43, are related to each other.

Turning back to FIG. 1, controller 1d identifies color information, which represents a color that is most similar to the color detected by detector 1b, from color information 1c3 in DB 1c. Controller 1d also reads gas identifying information 1c2, which is related to the identified color information 1c3, from DB 1c. Controller 1d handles the gas identifying information 1c2 as gas identifying information indicative of the gas to be identified.

Controller 1d includes color change detector 1d1 and gas identifier 1d2.

Color change detector 1d1 detects a change from the color of medium 43 before reagent 41 flows into medium 43 to the color of medium 43 after reagent 41 chemically reacts with a gas in accordance with the detected result from detector 1b. In the present embodiment, color change detector 1d1 detects the spectrum of the change in the color of medium 43 in accordance with the detected result from detector 1b.

Color change detector 1d1 includes spectrum detector 1d1a and memory 1d1b.

Spectrum detector 1d1a detects the spectrum of a change in the color of medium 43 in accordance with an output signal from processor 1b4.

Memory 1d1b stores the spectrum of the change in the color of medium 43 which has been detected by spectrum detector 1d1a.

FIG. 5 shows details of memory 1d1b.

As shown in FIG. 5, memory 1d1b stores the numbers of photodetectors λ of CCD 1b3, detected values S0, S1, SX from detector 1b, relative intensity (spectral data) S, binning relative intensity (spectral data) Sb, and band values Λ in relation to each other.

S0, S1, SX, S, Sb and Λ shown in FIG. 5 will be described in detail below.

When input unit 1a receives a dark-current measuring instruction before reagent 41 flows into medium 43, input unit 1a supplies the dark-current measuring instruction to spectrum detector 1d1a.

When spectrum detector 1d1a receives the dark-current measuring instruction from input unit 1a, spectrum detector 1d1a measures output signals S0(λ) from respective photodetectors λ of CCD 1b3 when light-emitting element 1b1 emit no light. Spectrum detector 1d1a stores measured output signals S0(λ) at S0 in memory 1d1b.

Then, when input unit 1a receives a light-emitting instruction before reagent 41 flows into medium 43, input unit 1a supplies the light-emitting instruction to light-emitting element 1b1 and spectrum detector 1d1a.

Upon receipt of the light-emitting instruction, light-emitting element 1b1 emits and applies light to medium 43.

Medium 43 reflects the light applied from light-emitting element 1b1. The light reflected by medium 43 represents the color (reflected intensity) of medium 43 before reagent 41 flows into medium 43. The reflected light is detected by photodetectors λ of CCD 1b3 through filter 1b2. Therefore, CCD 1b3 produces an output signal representing the spectrum of the reflected light.

When spectrum detector 1d1a receives the light-emitting instruction from input unit 1a after receiving the dark-current measuring instruction, spectrum detector 1d1a measures output signals from respective photodetectors λ of CCD 1b3, or in other words, output signals S1(λ) representing the spectrum of the color of medium 43 before reagent 41 flows into medium 43. Spectrum detector 1d1a stores output signals S1(λ) at S1 in memory 1d1b.

Thereafter, when ampule 42 of gas detecting device 4 is broken, reagent 41 contained in ampule 42 flows into medium 43. When reagent 41 flows into medium 43, reagent 41 chemically reacts with the gas to be identified which is held in contact with medium 43.

When input unit 1a receives a light-emitting instruction again after reagent 41 has flowed into medium 43, input unit 1a supplies the light-emitting instruction to light-emitting element 1b1 and spectrum detector 1d1a.

Upon receipt of the light-emitting instruction, light-emitting element 1b1 emits and applies light to medium 43.

Medium 43 reflects the light applied from light-emitting element 1b1. The light reflected by medium 43 represents the color (reflected intensity) of reagent 41 which has chemically reacted with the gas to be identified. Specifically, the reflected light represents the color (reflected intensity) of medium 43 which contains reagent 41 which has chemically reacted with the gas to be identified.

The reflected light is detected by photodetectors λ of CCD 1b3 through filter 1b2. Therefore, CCD 1b3 produces an output signal representing the spectrum of the reflected light.

When spectrum detector 1d1a receives the light-emitting instruction again from input unit 1a, spectrum detector 1d1a measures output signals from respective photodetectors λ of CCD 1b3, or in other words, output signals SX(λ) representing the spectrum of the color of medium 43 after reagent 41, which has flowed into medium 43, has chemically reacted with the gas to be identified. Spectrum detector 1d1a stores output signals SX(λ) at SX in memory 1d1b.

After having stored output signals SX(λ) in memory 1d1b, spectrum detector 1d1a calculates relative intensities S(λ) according to the following equation:

$$S(\lambda)=(SX(\lambda)-S0(\lambda))/(S1(\lambda)-S0(\lambda))$$

If the quality of medium 43 is stable, then S0(λ) and S1(λ) may be measured once and may be used in subsequent measuring cycles. In this case, it is possible to reduce the amount of processing for calculating relative intensities S(λ).

Spectrum detector 1d1a stores relative intensities S(λ) at S in memory 1d1b.

For storing color information into DB 1c, the same processing sequence as described above is carried out while medium 43 is being held in contact with a gas to be identified by the gas identifying information. Relative intensities S(λ) calculated at this time are stored as color information related to the gas identifying information in DB 1c.

After having stored relative intensities S(λ) in memory 1d1b, spectrum detector 1d1a calculates binning relative intensities (spectral data) Sb(Λ) based on a binning instruction supplied from input unit 1a.

For example, if the binning instruction indicates "4", then spectrum detector 1d1a adds four relative intensities S(λ) into binning relative intensity Sb(Λ). In the example shown in FIG. 5, spectrum detector 1d1a adds relative intensities S(1)-S(4) into binning relative intensity Sb(Λ=1), and adds relative intensities S(253)-S(256) into binning relative intensity Sb(Λ=64).

Spectrum detector 1d1a stores binning relative intensity Sb(Λ) at Sb(Λ) in memory 1d1b. Thereafter, spectrum detector 1d1a supplies binning relative intensity Sb(Λ) to gas identifier 1d2.

Upon receipt of the binning instruction from input unit 1a, spectrum detector 1d1a calculates bands (Λ) in accordance with the binning instruction, and stores calculated bands (Λ) at Λ in memory 1d1b.

Gas identifier 1d2 identifies color change information, which represents a change in the color which is most similar to the change in the color of medium 43 that is detected by color change detector 1d1, from color change information 1c3 stored in DB 1c.

For example, gas identifier 1d2 identifies spectral information, which represents a spectrum which is most similar to the spectrum representing the change in the color of medium 43 that is detected by spectrum detector 1d1a, from color information 1c3 in DB 1c.

In the present embodiment, gas identifier 1d2 identifies spectral information, which represents a spectral waveform that is most similar to the waveform of the spectrum representing the change in the color of medium 43 that is detected by spectrum detector 1d1a, and which also represents a spectral waveform whose degree of conformity with the waveform of the spectrum representing the change in the color of medium 43 is a predetermined value or greater, from color information 1c3 in DB 1c.

Specifically, gas identifier 1d2 performs the following processing sequence:

Gas identifier 1d2 places spectrum Sb(Λ), which indicates the change in the color of medium 43 which is detected by spectrum detector 1d1a, hypothetically in a multidimensional space where each band (Λ) represents coordinates. Therefore, spectrum Sb(Λ) is represented as a vector in the multidimensional space.

Gas identifier 1d2 processes each spectral information stored in DB 1c in accordance with the binning instruction supplied from input unit 1a to equalize the number of bands of each spectral information to the number of bands in spectrum Sb(Λ).

For example, if the binning instruction indicates "4", then gas identifier 1d2 puts together four items of spectral information of a gas to be identified by gas identifying information 1c2 to equalize the number of bands of each spectral information in DB 1c to the number of bands in spectrum Sb(Λ).

Gas identifier 1d2 places each spectral information, whose number of bands is the same as that of spectrum Sb(Λ), hypothetically in a multidimensional space where each band (Λ) represents coordinates. Therefore, each spectral information is represented as a vector in the multidimensional space.

Gas identifier 1d2 calculates an inner product of spectrum Sb(Λ) and each spectral information, and selects spectral information whose angle with respect to spectrum Sb(Λ) is the smallest, based on the value of the calculated inner product. Such a process is known as Spectral Angle Mapper (SAM).

The angle between spectrum Sb(Λ) and spectral information is smaller as their spectral waveforms are closer to each other. Stated otherwise, the angle between spectrum Sb(Λ) and the spectral information represents the degree of conformity therebetween.

Then, gas identifier 1d2 determines whether or not the angle between spectrum Sb(Λ) and the selected spectral information is equal to or smaller than a predetermined angle.

If the angle between spectrum Sb(Λ) and the selected spectral information is equal to or smaller than the predetermined angle, then gas identifier 1d2 identifies the selected spectral information as spectral information representing spectrum Sb(Λ).

Then, gas identifier 1d2 reads gas identifying information related to the identified spectral information from DB 1c.

Gas identifier 1d2 supplies the read gas identifying information, as gas identifying information representing the gas to be identified, to display unit 1g and communication unit 1h.

GPS 1e is an example of position output unit. GPS 1e generates positional information representing the present position of gas identifying apparatus 1, and supplies the generated positional information to gas identifier 1d2.

Memory 1f stores identification information (ID) of gas identifying apparatus 1. The ID is read by gas identifier 1d2.

In the present embodiment, gas identifier 1d2 supplies the gas identifying information 1c2 that is read from DB 1c, the positional information that is supplied from GPS 1e, and the ID that is read from memory 1f, to display unit 1g and communication unit 1h.

When display unit 1g receives gas identifying information 1c2, the positional information, and the ID from gas identifier 1d2, display unit 1g displays gas identifying information 1c2, the positional information, and the ID.

When communication unit 1h receives gas identifying information 1c2, the positional information, and the ID from gas identifier 1d2, communication unit 1h sends gas identifying information 1c2, the positional information, and the ID to information center 2.

Information center 2 communicates with gas identifying apparatus 1 and handling center 3.

Communication unit 2a communicates with communication unit 1h of gas identifying apparatus 1 and communication unit 3a of handling center 3.

Handling information storage unit 2b stores the gas identifying information and handling information representing how to handle a gas that is identified by the gas identifying information, in relation to each other.

FIG. 6 shows an example of handling information storage unit 2b.

As shown in FIG. 6, handling information storage unit 2b stores gas identifying information 2b1 and handling information 2b2, in relation to each other.

Referring back to FIG. 1, handling center storage unit 2c stores handling center information representing handling center 3, e.g., the name of handling center 3 and its contact address, and the territory covered by handling center 3, in relation to each other.

FIG. 7 shows an example of handling center storage unit 2c.

As shown in FIG. 7, handling center storage unit 2c stores handling center information 2c1 and territory 2c2 in relation to each other.

Referring back to FIG. 1, center controller 2d controls operation of information center 2.

For example, when communication unit 2a receives gas identifying information 1c2, the positional information, and the ID, center controller 2d displays gas identifying information 1c2, the positional information, and the ID on display unit 2e.

Center controller 2d reads handling information related to the gas identifying information from handling information storage unit 2b. Center controller 2d displays the handling information on display unit 2e.

Center controller 2d identifies a handling center whose territory includes the position indicated by the positional information received by communication unit 2a, by referring to handling center storage unit 2c. Specifically, center controller 2d selects a territory that includes the position indicated by the positional information, from territories stored in handling center storage unit 2c, and identifies handling center information related to the selected territory.

Center controller 2d controls communication unit 2a to send the gas identifying information, the positional information, the ID, and the handling information to the handling center that has been identified.

Display unit 2e is controlled by center controller 2d to display various pieces of information.

Handling center 3 may be a police station, a fire station, or a medical facility, for example.

Communication unit 3a receives the gas identifying information, the positional information, and the handling information sent from communication unit 2a of information center 2.

Controller 3b supplies the gas identifying information, the positional information, and the handling information received by communication unit 3a to display unit 3c.

Display unit 3c displays the gas identifying information, the positional information, and the handling information supplied from controller 3b.

Operation of the gas handling assisting system will be described below.

Figure 8:
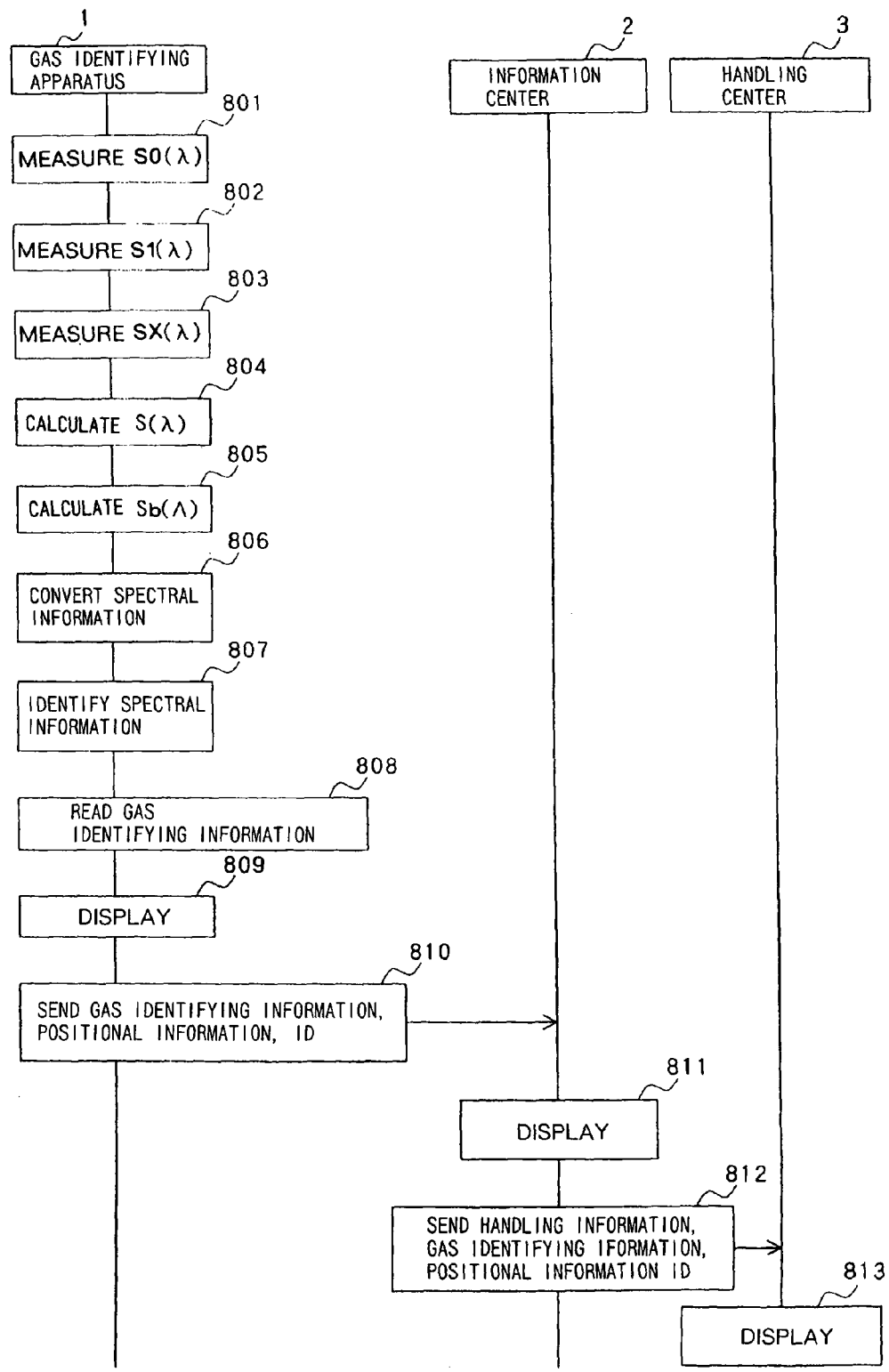
FIG. 8 is a sequence diagram illustrative of operation of the gas handling assisting system.

FIG. 8 is a sequence diagram illustrative of operation of the gas handling assisting system. Operation of the gas handling assisting system will be described below with reference to FIG. 8. Those parts in FIG. 8 which are identical to those shown FIG. 1 are denoted by identical reference characters in FIG. 8.

It is assumed in the operation to be described below that the user enters a binning instruction indicating "binning=4" into input unit 1a. However, a binning instruction is not limited to "binning=4", but may be changed as desired.

First, the user moves frame 1i so that gas detecting device 4 is placed in frame 1i before reagent 41 flows into medium 43. At this time, ambient light should not be introduced into frame 1i.

Then, the user enters a dark-current measuring instruction into input unit 1a. When input unit 1a accepts the dark-current measuring instruction, step 801 (see FIG. 8) is carried out.

In step 801, input unit 1a supplies the dark-current measuring instruction to spectrum detector 1d1a.

When spectrum detector 1d1a receives the dark-current measuring instruction, spectrum detector 1d1a measures output signals S0(λ) from respective photodetectors λ of CCD 1b3 when no light is emitted from light-emitting element 1b1.

Then, spectrum detector 1d1a stores measured output signals S0(λ) at S0 in memory 1d1b.

Step 801 is now over.

Then, the user enters a light-emitting instruction into input unit 1a. When input unit 1a accepts the light-emitting instruction, step 802 is carried out.

In step 802, input unit 1a supplies the light-emitting instruction to light-emitting element 1b1 and spectrum detector 1d1a.

Upon receipt of the light-emitting instruction, light-emitting element 1b1 applies light to medium 43 of gas detecting device 4.

Medium 43 reflects the light applied from light-emitting element 1b1. The light reflected by medium 43 represents the color (reflected intensity) of medium 43 before reagent 41 flows into medium 43. The reflected light is detected by photodetectors λ of CCD 1b3 through filter 1b2. Therefore, CCD 1b3 produces an output signal representing the spectrum of the reflected light.

When spectrum detector 1d1a receives the light-emitting instruction from input unit 1a after it has received the dark-current measuring instruction, spectrum detector 1d1a measures output signals from respective photodetectors λ of CCD 1b3, or in other words, output signals S1(λ) representing the spectrum of the color of medium 43 before reagent 41 flows into medium 43. Spectrum detector 1d1a stores output signals S1(λ) at S1 in memory 1d1b.

Step 802 is now over.

Then, the user breaks ampule 42 of gas detecting device 4.

When ampule 42 is broken, reagent 41 contained in ampule 42 flows into medium 43. When reagent 41 flows into medium 43, reagent 41 chemically reacts with the gas to be identified which is held in contact with medium 43.

Then, the user enters a light-emitting instruction again into input unit 1a. When input unit 1a accepts the light-emitting instruction again, step 803 is carried out.

In step 803, input unit 1a supplies the light-emitting instruction to light-emitting element 1b1 and spectrum detector 1d1a.

When light-emitting element 1b1 receives the light-emitting instruction, light-emitting element 1b1 applies light to medium 43.

Medium 43 reflects the light applied from light-emitting element 1b1. The light reflected by medium 43 represents the color (reflected intensity) of reagent 41 that has chemically reacted with the gas to be identified. Specifically, the reflected light represents the color (reflected intensity) of medium 43 which contains reagent 41 which has chemically reacted with the gas to be identified.

The reflected light is detected by photodetectors λ of CCD 1b3 through filter 1b2. Therefore, CCD 1b3 produces an output signal representing the spectrum of the reflected light.

When spectrum detector 1d1a receives the light-emitting instruction again from input unit 1a, spectrum detector 1d1a measures output signals from respective photodetectors λ of CCD 1b3, or in other words, output signals SX(λ) representing the spectrum of the color of medium 43 after reagent 41, which has flowed into medium 43, has chemically reacted with the gas to be identified. Spectrum detector 1d1a stores output signals SX(λ) at SX in memory 1d1b.

Step 803 is now over.

After spectrum detector 1d1a has stored output signals SX(λ) at SX in memory 1d1b, spectrum detector 1d1a executes step 804.

In step 804, spectrum detector 1d1a calculates relative intensities S(λ) according to the following equation:

$$S(\lambda)=(SX(\lambda)-S0(\lambda))/(S1(\lambda)-S0(\lambda))$$

Spectrum detector 1d1a stores relative intensities S(λ) at S in memory 1d1b. Having stored relative intensities S(λ) in memory 1d1b, spectrum detector 1d1a executes step 805.

In step 805, spectrum detector 1d1a calculates binning relative intensities (spectral data) Sb(Λ) in accordance with a binning instruction supplied from input unit 1a.

Since the binning instruction indicates "4", then spectrum detector 1d1a adds four relative intensities S(λ) into binning relative intensity Sb(Λ).

Spectrum detector 1d1a stores binning relative intensity Sb(Λ) at Sb(Λ) in memory 1d1b. Thereafter, spectrum detector 1d1a supplies binning relative intensity Sb(Λ) to gas identifier 1d2.

When gas identifier 1d2 receives binning relative intensity Sb(Λ), steps 806, 807 are carried out using SAM.

In steps 806, 807, gas identifier 1d2 identifies spectral information representing a spectral waveform that is most similar to the waveform Sb(Λ) of the spectrum representing the change in the color of medium 43 that is detected by spectrum detector 1d1a, and also representing a spectral waveform whose degree of conformity with the waveform of the spectrum representing the change in the color of medium 43 is a predetermined value or greater, from spectral information 1c3 stored in DB 1c.

Specifically, gas identifier 1d2 performs the following process:

Gas identifier 1d2 executes step 806.

In step 806, gas identifier 1d2 places spectrum Sb(Λ) indicative of the change in the color of medium 43 which is detected by spectrum detector 1d1a, hypothetically in a multidimensional space where each band (Λ) represents coordinates.

Gas identifier 1d2 processes each spectral information stored in DB 1c based on the binning instruction supplied from input unit 1a to equalize the number of bands of each spectral information to the number of bands in spectrum Sb(Λ).

As the binning instruction indicates "4", gas identifier 1d2 puts together four items of spectral information of a gas to be identified by gas identifying information 1c2 to equalize the number of bands of each spectral information in DB 1c to the number of bands in spectrum Sb(Λ).

Gas identifier 1d2 places each spectral information whose number of bands is the same as that of spectrum Sb(Λ), hypothetically in a multidimensional space where each band (Λ) represents coordinates.

Having placed each spectral information hypothetically in the multidimensional space, gas identifier 1d2 executes step 807.

In step 807, gas identifier 1d2 calculates an inner product of spectrum Sb(Λ) and each spectral information, and selects spectral information whose angle with respect to spectrum Sb(Λ) is the smallest, based on the value of the calculated inner product.

Then, gas identifier 1d2 determines whether or not the angle between spectrum Sb(Λ) and the selected spectral information is equal to or smaller than a predetermined angle.

If the angle between spectrum Sb(Λ) and the selected spectral information is equal to or smaller than the predetermined angle, then gas identifier 1d2 identifies the spectral information as spectral information representing spectrum Sb(Λ).

Figure 9:
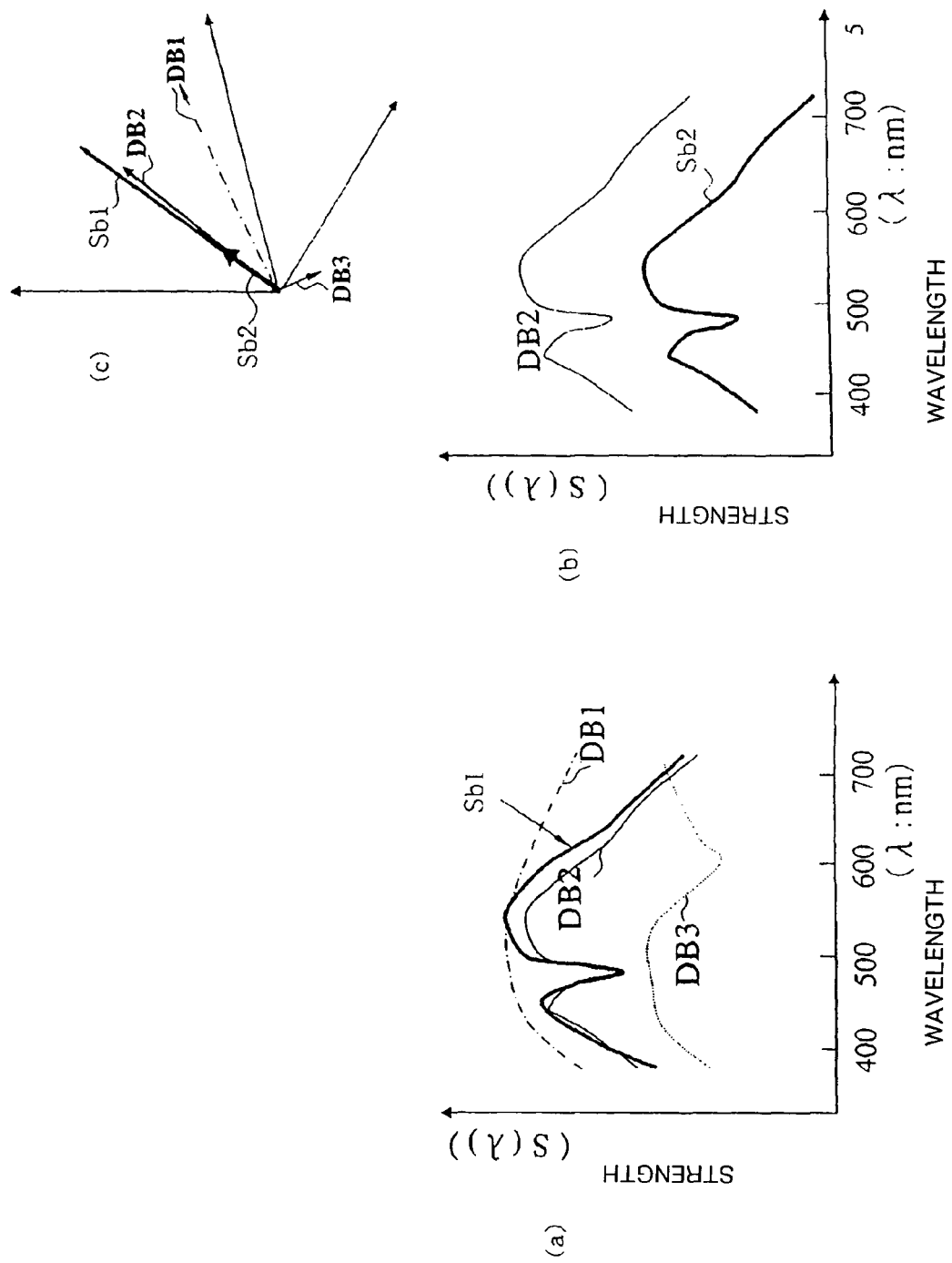
FIGS. 9(a) through (c) are diagrams showing a process of identifying spectral information using SAM.

FIGS. 9(a) through (c) are diagrams showing a process of identifying spectral information using SAM.

In FIGS. 9(a) through (c), DB1 represents the spectral waveform of spectral information related to gas identifying information a, DB2 represents the spectral waveform of spectral information related to gas identifying information b, and DB3 represents the spectral waveform of spectral information related to gas identifying information c.

In FIG. 9(a), Sb1 represents measured spectrum Sb1 whose waveform and intensity are similar to DB2. In FIG. 9(b), Sb2 represents measured spectrum Sb2 whose waveform is identical to DB2 and whose intensity is different from DB2.

The degree of conformity between spectral waveforms represents the degree of conformity between chemical reactions.

However, the degree of conformity between intensities does not necessarily represent the degree of conformity between chemical reactions. The reasons for this are that the intensity of a chemical reaction varies depending on the ambient temperature and humidity at the time of the chemical reaction and also on the concentration of the gas.

Therefore, it is preferable to identify spectral information corresponding to the measured spectrum by determining whether spectral waveforms are in conformity with each other or not.

In the present invention, spectral information is identified using SAM. Consequently, spectral information corresponding to the measured spectrum is identified in accordance with the degree of conformity between spectral waveforms.

FIG. 9(c) shows DB1, DB2, DB3, Sb1 and Sb2 that are placed in the same multidimensional space.

As shown in FIG. 9(c), the angle between Sb1 and DB2 whose spectral waveforms are similar to each other is small, and the angle between Sb2 and DB2 whose spectral waveforms are similar to each other is also small.

According to the present embodiment, therefore, it is possible to identify spectral information corresponding to the measured spectrum not only when spectral waveforms and intensities are similar as shown in FIG. 9(a), but also when spectral waveforms are similar, but intensities are different, as shown in FIG. 9(b).

After having identified spectral information indicative of spectrum Sb(Λ), gas identifier 1d2 executes step 808.

In step 808, gas identifier 1d2 reads gas identifying information 1c2 related to the identified spectral information from DB 1c.

Gas identifier 1d2 supplies gas identifying information 1c2, positional information supplied from GPS 1e, and ID read from memory 1f to display unit 1g and communication unit 1h.

When display unit 1g receives gas identifying information 1c2, the positional information, and the ID from gas identifier 1d2, display unit 1g executes step 809.

In step 809, display unit 1g displays gas identifying information 1c2, the positional information, and the ID.

When communication unit 1h receives gas identifying information 1c2, the positional information, and the ID from gas identifier 1d2, communication unit 1h executes step 810.

In step 810, communication unit 1h sends gas identifying information 1c2, the positional information, and the ID to information center 2.

When communication unit 2a of information center 2 receives gas identifying information 1c2, the positional information, and the ID, step 811 is executed.

In step 811, center controller 2d reads handling information related to the gas identifying information from handling information storage unit 2b. Center controller 2d displays the handling information, the gas identifying information, the positional information, and the ID on display unit 2e. Accordingly, information center 2 can instruct personnel to perform a hazard prevention process for evacuation, hazardous gas neutralization, etc.

After having displayed the gas identifying information, etc. on display unit 2e, center controller 2d executes step 812.

In step 812, center controller 2d selects a territory that includes the position indicated by the positional information, from territories stored in handling center storage unit 2c, and identifies handling center information related to the selected territory.

Center controller 2d controls communication unit 2a to send the gas identifying information, the positional information, the ID, and the handling information to the handling center that has been identified.

When communication unit 3a of the handling center 3 receives the gas identifying information, the positional information, the ID, and the handling information sent from communication unit 2a of information center 2, step 813 is executed.

In step 813, controller 3b supplies the gas identifying information, the positional information, and the handling information received by communication unit 3a to display unit 3c. Display unit 3c then displays the gas identifying information, the positional information, and the handling information supplied from controller 3b.

According to the present invention, controller 1d identifies color information representing a color which is most similar to the color of reagent 41 that has chemically reacted with the gas to be identified, from the color information stored in DB 1c, and reads gas identifying information related to the identified color information from DB 1c.

Therefore, if gas identifying information and color information related to the gas to be identified are stored in DB 1c, then the gas can be identified with high accuracy without the need for a decision by the user. It is thus possible to identify the gas with high accuracy in accordance with the color of reagent 41 which has changed by the chemically reaction with the gas.

According to the present embodiment, furthermore, when reagent 41 flows into medium 43 that is held in contact with the gas to be identified, reagent 41 chemically reacts with the gas.

DB 1c stores, as color information, color change information representing a change from the color of medium 43 before reagent 41 flows into medium 43 to the color of medium 43 after reagent 41 chemically reacts with the gas.

Detector 1b detects the color of medium 43 before reagent 41 flows into medium 43 and the color of medium 43 after reagent 41 flows into medium 43 and chemically reacts with the gas.

Color change detector 1d1 detects a change in the color of medium 43 in accordance with the detected result from detector 1b.

Gas identifier 1d2 identifies color change information representing a change in the color which is most similar to the detected change in the color of medium 43, from the color change information stored in DB 1c, and reads gas identifying information related to the identified color change information from DB 1c.

The gas to be identified is identified based on the change in the color of the medium. The change in the color of the medium represents the type of the gas that has chemically reacted with the reagent. Therefore, the gas to be identified can be identified highly accurately.

According to the present embodiment, DB 1c stores spectral information representing a spectrum indicative of a change in the color of medium 43, as color change information.

Detector 1d detects the spectrum of the color of medium 43 before reagent 41 flows into medium 43 and the spectrum of the color of medium 43 after reagent 41 flows into medium 43 and chemically reacts with the gas to be identified.

Color change detector 1d1 detects the spectrum of the change in the color of medium 43 in accordance with the detected result from detector 1b.

Gas identifier 1d2 identifies spectral information, which represents a spectrum which is most similar to the spectrum representing the detected change in the color of the medium, from the color information stored in DB 1c, and reads gas identifying information related to the identified spectral information from DB 1c.

The change in the color of medium 43 is identified by the spectrum. Therefore, the gas to be identified can be identified highly accurately.

According to the present embodiment, gas identifier 1d2 identifies spectral information representing a spectral waveform that is most similar to the waveform of the spectrum representing the detected change in the color of medium 43, and also representing a spectral waveform whose degree of conformity with the waveform of the spectrum representing the change in the color of medium 43 is of a predetermined value or greater, from the spectral information stored in DB 1c, and reads gas identifying information related to the identified spectral information from DB 1c.

Therefore, the gas to be identified can be identified highly accurately.

According to the present embodiment, DB 1c stores color information depending on the detected result from detector 1b when detector 1b detects the color of reagent 41 which has chemically reacted with the gas identified by the gas identifying information.

The color information in the DB 1c depends on the characteristics of the detector. Therefore, it is possible to easily match the color information in the DB 1c and the detected result from the detector.

According to the present embodiment, communication unit 1h sends the gas identifying information that is read by controller 1d to information center 2.

Therefore, the information of the identified gas can automatically be sent to information center 2.

According to the present embodiment, communication unit 1h sends positional information representative of the present position, together with the gas identifying information, to information center 2.

Therefore, information as to the position where the identified gas is present can automatically be sent to information center 2.

According to the present embodiment, information center 2 displays the gas identifying information and the positional information that is sent from gas identifying apparatus 1. Therefore, information center 2 is able to let the user of information center 2 know the occurrence of the gas, or the occurrence of the gas and the location where the gas is occurring.

According to the present embodiment, information center 2 reads handling information related to the received gas identifying information from handling information storage unit 2b, and displays the handling information.

Therefore, the user of information center 2 can be notified of details of how to handle the gas that is occurring.

According to the present embodiment, information center 2 identifies a handling center whose territory includes the position indicated by the received positional information, by referring to handling center storage unit 2c, and sends the positional information and the handling information to the identified handling center.

Therefore, handling center 3 whose territory covers the location where the gas is occurring can be notified of the location where the gas is occurring and the details of how to handle the occurring gas.

In the above embodiment, the user enters the dark-current measuring instruction, the light-emitting instruction, and the binning instruction. However, controller 1d may automatically generate these instructions in sequential order. For example, controller 1d may execute a program representing a time sequence for automatically generating these instructions in sequential order, thereby automatically generating these instructions in sequential order.

A second embodiment of the present invention will be described below.

Figure 10:
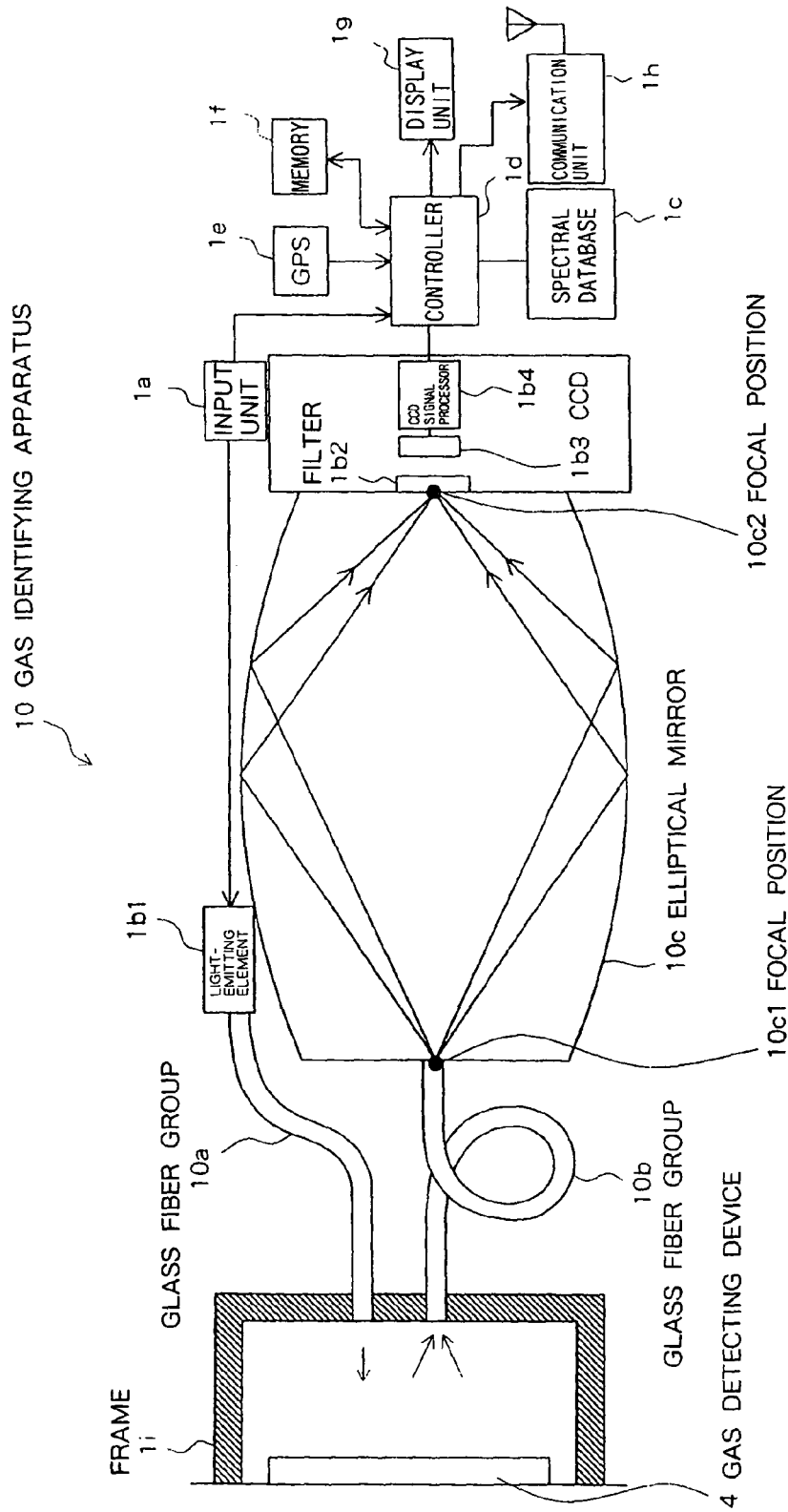
FIG. 10 is a block diagram of a gas identifying apparatus according to a second embodiment of the present invention.

FIG. 10 shows gas identifying apparatus 10 according to a second embodiment of the present invention in block form. Those parts in FIG. 10 which are identical to those shown FIG. 1 are denoted by identical reference characters in FIG. 10.

Gas identifying apparatus 10 shown in FIG. 10 includes glass fiber groups 10a, 10b and elliptical mirror 10c, unlike gas identifying apparatus 1 shown in FIG. 1.

Glass fiber group 10a is an example of emitted-light guiding optical fiber for guiding light emitted from light-emitting element 1b1 to frame 1i.

Glass fiber group 10b is an example of reflected-light guiding optical fiber for guiding light reflected by medium 43 of gas detecting device 4 to focal position 10c1 of elliptical mirror 10c.

Elliptical mirror 10c is an example of light guide, with filter 1b2 disposed at other focal position 10c2 thereof.

Since the reflected light is guided to focal position 10c1 and filter 1b2 is disposed at other focal position 10c2, elliptical mirror 10c guides the reflected light, which is received from glass fiber group 10b, to filter 1b2.

Figure 11:
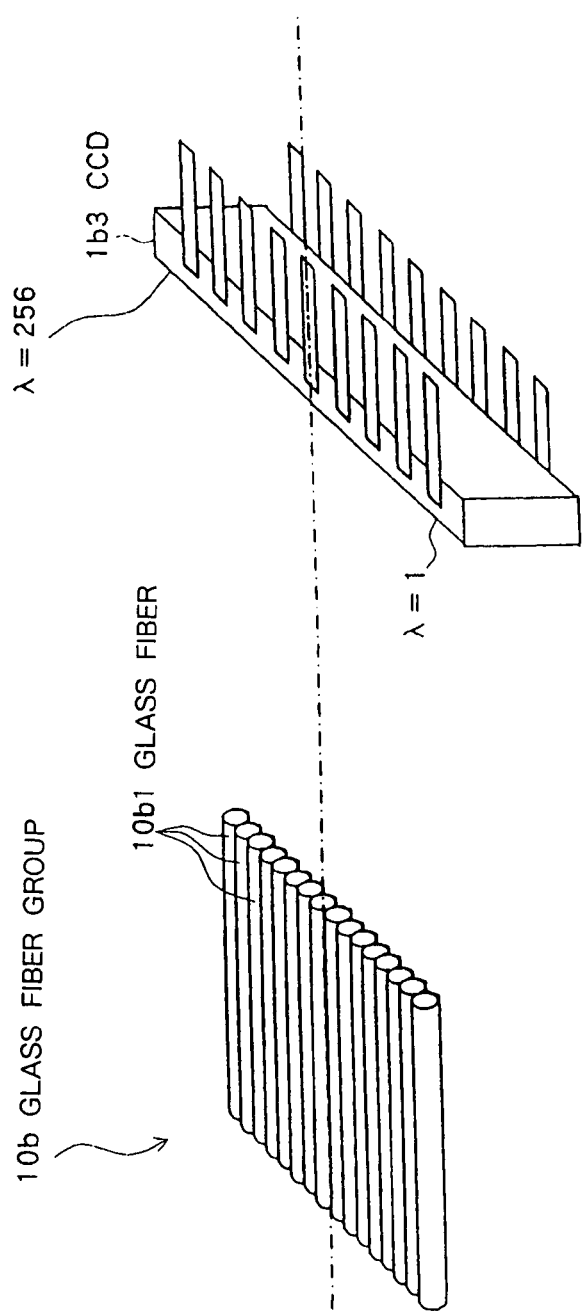
FIG. 11 is a perspective view showing the positional relationship between a glass fiber group and a CCD of the gas identifying apparatus shown in FIG. 10.

FIG. 11 illustrates the positional relationship between glass fiber group 10b and CCD 1b3. Those parts in FIG. 11 which are identical to those shown FIG. 10 are denoted by identical reference characters in FIG. 11.

As shown in FIG. 11, glass fiber group 10b comprises an array of glass fibers 10b1 arranged in the same direction as the photodetectors of CCD 1b3.

According to the present embodiment, elliptical mirror 10c guides the light, which is applied from light-emitting element 1b1 and then reflected from medium 43, to filter 1b2 and CCD 1b3. Therefore, filter 1b2 and CCD 1b3 are capable of reliably receiving and detecting the reflected light.

According to the present embodiment, glass fiber group 10a guides the light applied from light-emitting element 1b1 to medium 43, and glass fiber group 10b guides the light reflected from medium 43 to elliptical mirror 10c. Therefore, detector 1b and gas detecting device 4 including reagent 41 can be connected to each other by glass fiber groups 10a and 10b. Gas detecting device 4 and detector 1b can thus be spaced from each other. For example, the user may wear a unit including detector 1b, etc. on the waist, and may operate frame 1i such that gas detecting device 4 will be housed in frame 1i.

Elliptical mirror 10c guides the reflected light guided by glass fiber group 10b to filter 1b2 and CCD 1b3. Therefore, even if the direction along which the reflected light guided by glass fiber group 10b may not be constant due to a flexing of glass fiber group 10b, filter 1b2 and CCD 1b3 are capable of reliably receiving and detecting the reflected light.

A third embodiment of the present invention will be described below.

Figure 12:
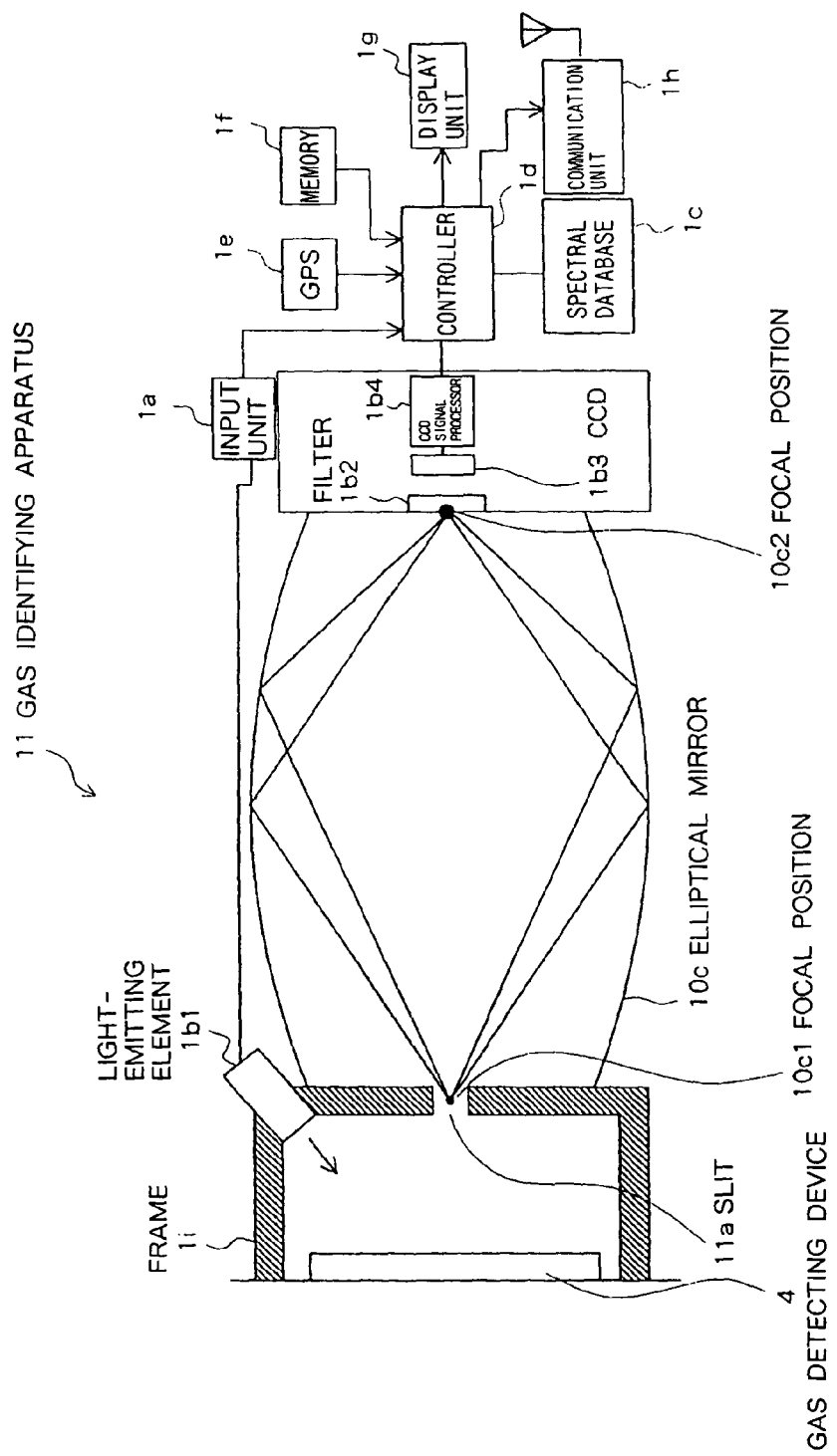
FIG. 12 is a block diagram of a gas identifying apparatus according to a third embodiment of the present invention.

FIG. 12 shows gas identifying apparatus 11 according to a third embodiment of the present invention in block form. Those parts in FIG. 12 which are identical to those shown FIG. 10 are denoted by identical reference characters in FIG. 12.

Gas identifying apparatus 11 shown in FIG. 12 includes slit 11a, rather than glass fiber groups 10a and 10b, unlike gas identifying apparatus 10 shown in FIG. 10.

Slit 11*a* is disposed at focal position 10*c*1 of elliptical mirror 10*c*, and passes therethrough the light reflected by medium 43.

Figure 13:
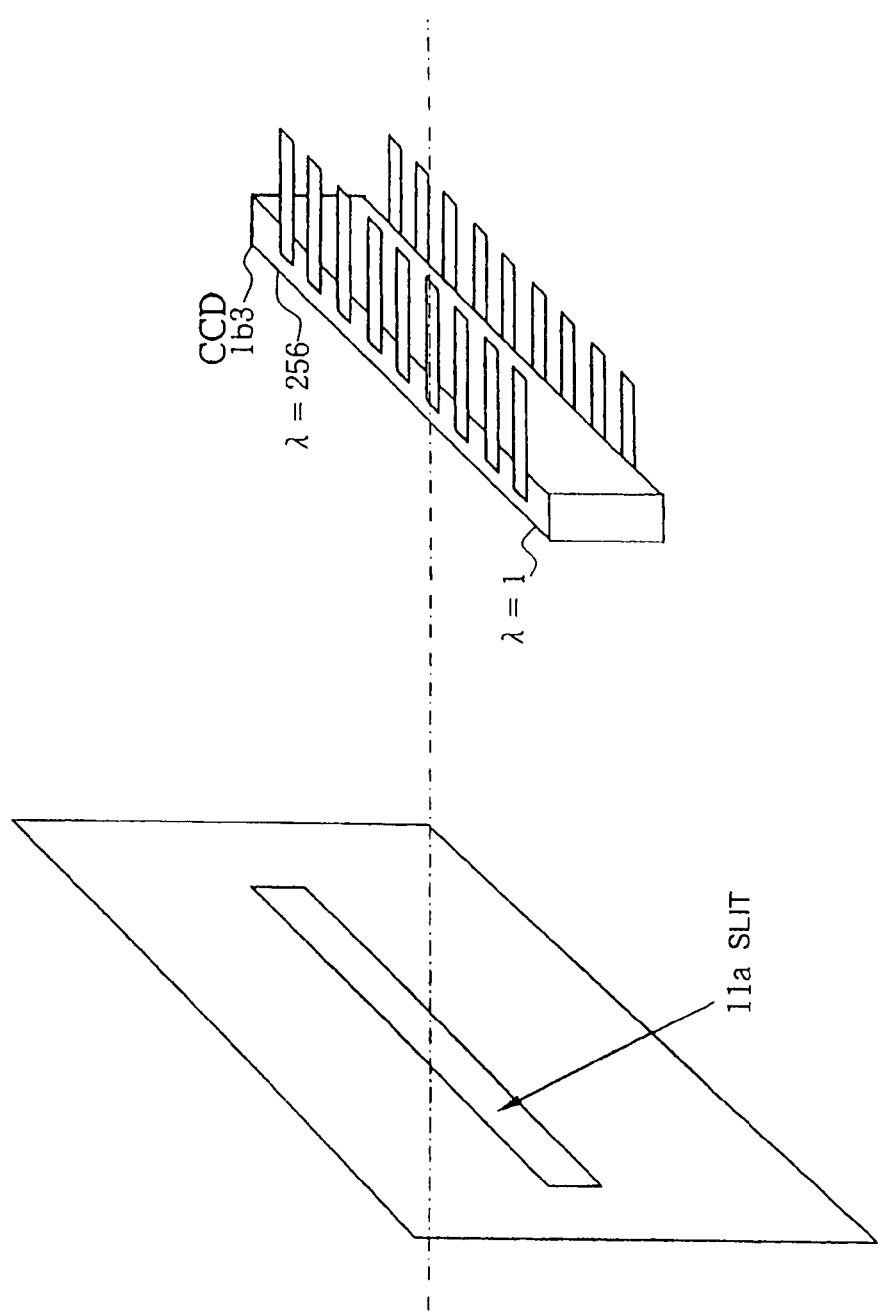
FIG. 13 is a perspective view showing the positional relationship between a slit and a CCD of the gas identifying apparatus shown in FIG. 12.

FIG. 13 illustrates the positional relationship between slit 11*a* and CCD 1*b*3. Those parts in FIG. 13 which are identical to those shown FIG. 12 are denoted by identical reference characters in FIG. 13.

As shown in FIG. 13, slit 11*a* has its longitudinal axis extending in the same direction as the photodetectors of CCD 1*b*3.

According to the present embodiment, slit 11*a* and elliptical mirror 10*c* make it possible for filter 1*b*2 and CCD 1*b*3 to reliably receive and detect the light that is applied from light-emitting element 1*b*1 and then reflected from medium 43.

In each of the above embodiments, DB 1*c* and controller 1*d* should preferably be arranged as follows:

DB 1*c* stores gas identifying information, and absorption lines obtained from the spectrum of the color of reagent 41 that has chemically reacted with the gases to be identified by the gas identifying information, in relation to each other.

Controller 1*d* identifies an absorption line of a material which is produced due to a chemical reaction between a gas to be identified and reagent 41, using the color detected by detector 1*b*. Controller 1*d* then identifies an absorption line, which is closest to the identified absorption line, from the absorption lines stored in DB 1*c*. Thereafter, controller 1*d* reads gas identifying information related to the identified absorption line as gas identifying information representing the gas to be identified, from DB 1*c*.

Therefore, it is possible to identify the gas to be identified, in accordance with the absorption line of the material which is produced due to the chemical reaction between the medium, the gas and the reagent.

If gas detecting device 4 has a plurality of mediums 43 into which respective different reagents 41 will flow, then a plurality of gas identifying apparatus according to the present invention may be employed to simultaneously detect changes in the colors of reagents 41. Alternatively, a single gas identifying apparatus according to the present invention may be employed to sequentially detect changes in the colors of reagents 41, one at a time.

If gas identifier 1*d*2 is unable to identify a gas to be identified, then gas identifier 1*d*2 may control display unit 1*g* to display a prompt for breaking a next ampule.

Color information may be stored in DB 1*c* as follows:

The user pours a plurality of reagents into medium 43, which is held in contact with a given gas, according to a predetermined sequence, and detector 1*b* detects successive changes in the color of medium 43. DB 1*c* stores successively detected results from detector 1*b* as color information corresponding to the given gas (gas identifying information of the given gas).

In this case, controller 1*d* identifies a gas to be identified as follows:

The user pours a plurality of reagents into medium 43, which is held in contact with the gas to be identified, according to the above predetermined sequence, and detector 1*b* detects successive changes in the color of medium 43.

Each time detector 1*b* detects a change in the color of medium 43, controller 1*d* compares the detected result with the color information in DB 1*c*, and identifies color information which is most similar to the color detected by detector 1*b* from the color information in DB 1*c*. Controller 1*d* then reads gas identifying information related to the identified color information from DB 1*c*.

In each of the above embodiments, detector 1*b* may be modified as follows:

The photodetector unit including filter 1*b*2 and CCD 1*b*3 does not detect the light, which is applied from light-emitting element 1*b*1 and then reflected from medium 43, but detects light that is applied from light-emitting element 1*b*1 and then transmitted through medium 43.

Figure 14:
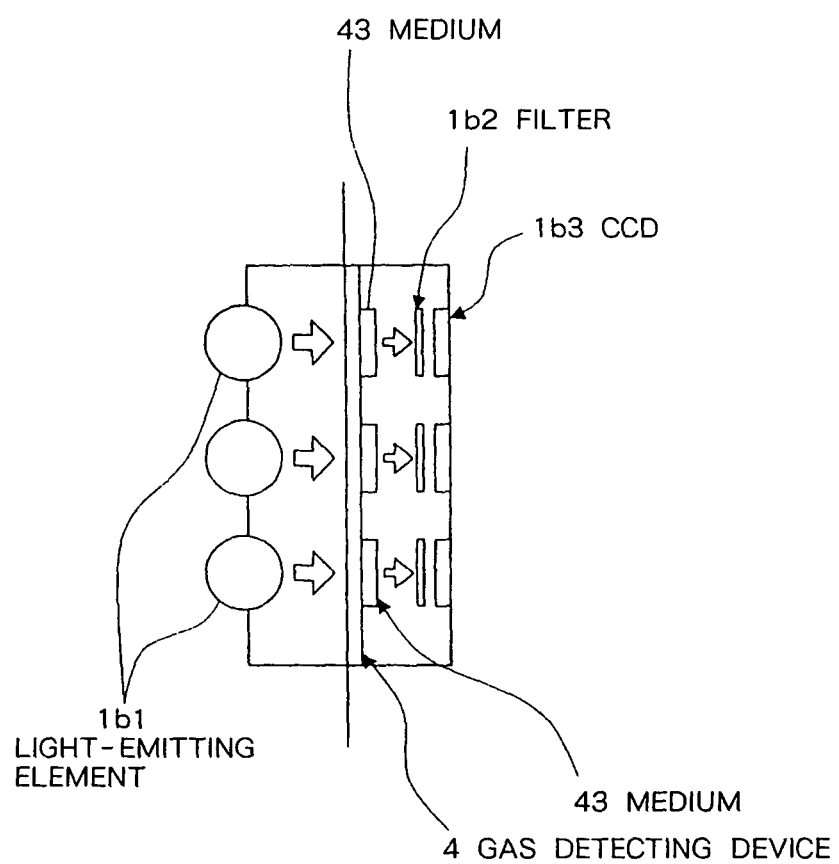
FIG. 14 is a view showing a modified gas detecting device.

FIG. 14 shows a modified detector 1*b*, or specifically a detector having filter 1*b*2 and CCD 1*b*3 for detecting light that is applied from light-emitting element 1*b*1 and then transmitted through medium 43. Those parts in FIG. 14 which are identical to those shown FIG. 1 are denoted by identical reference characters in FIG. 14.

Light-emitting element 1*b*1 applies light to medium 43. The light applied from light-emitting element 1*b*1 passes through medium 43. The light that has passed through medium 43 has the color of medium 43, and is detected by CCD 1*b*3 through filter 1*b*2.

The gas identifying apparatus according to the present invention may be incorporated in the reader disclosed in U.S. Pat. No. 6,228,657B1.

In each of the embodiments, the illustrated details are shown by way of example only, and the present invention should not be interpreted as being limited to the illustrated details.

For example, center controller 2*d* of information center 2 may control communication unit 2*a* to perform a process of sending handling information corresponding to gas identifying information to gas identifying apparatus 1 which has sent the gas identifying information.

With the above arrangement, the user of gas identifying apparatus 1 can appropriately handle the gas that has been identified by gas identifying apparatus 1.

While preferred embodiments of the present invention have been described using specific terms, such description is for illustrative purposes only, and it is to be understood that changes and variations may be made without departing from the spirit or scope of the following claims.

What is claimed is:

1. A gas identifying apparatus configured to identify a gas to be identified, said apparatus comprising:
   a gas detecting device configured so as to identify the gas to be identified in accordance with a color of a reagent which has chemically reacted with the gas to be identified;
   a database storing, in advance, gas identifying information which corresponds to a gas, and color information which corresponds to a color of a reagent chemically reacted with the gas, in relation to each other;
   a detector detecting the color of the reagent chemically reacted with the gas to be identified in said gas detecting device; and
   a controller identifying the color information which is most similar to the color detected by said detector, from the color information stored in said database, and reading the gas identifying information related to the identified color information from said database,
   wherein said reagent chemically reacts with the gas to be identified when the reagent flows into a medium that is held in contact with the gas to be identified in said gas detecting device,
   wherein said databases, as said color information, color change information representing a change from a color of said medium before said reagent flows into said medium to a color of said medium after said reagent flows into said medium and chemically reacts with the gas,
   wherein said detector detects the color of said medium before said reagent flows into said medium and the color of said medium after said reagent flows into said medium and chemically reacts with the gas, wherein said controller comprises:
    a color change detector detecting a change in the color of said medium in accordance with detected results from said detector; and
    a gas identifier identifying color change information, which is most similar to the change in the color of said medium which is detected by said color change detector, from the color change information stored in said database, and reading the gas identifying information related to the identified color change information said database, wherein said detector comprises:
    a light-emitting element applying light to said medium;
    an emitted-light guiding optical fiber guiding the light which is applied from said light-emitting element to said medium;
    a photodetector; and
    a light guided guiding the light, which is applied from said light-emitting element and then reflected from said medium, to said photodetector, said light guide including;
        an elliptical mirror; and
        reflected-light guiding optical fiber disposed at a focal position of the elliptical mirror, and wherein said photodetector is disposed at another focal position of said elliptical mirror.

2. The gas identifying apparatus according to claim 1, wherein said database stores, as said color change information, spectral information representing a spectrum indicative of the change in the color of said medium,
    wherein said detector detects a spectrum of the color of said medium before said reagent flows into said medium and a spectrum of the color of said medium after said reagent flows into said medium and chemically reacts with the gas,
    wherein said color change detector detects a spectrum indicative of the change in the color of said medium in accordance with detected results from said detector, and
    wherein said gas identifier identifies spectral information representing a spectrum, which is most similar to the spectrum representing the change in the color of said medium which is detected by said color change detector, from the spectral information stored in said database, and reads the gas identifying information related to the identified spectral information from said database.

3. The gas identifying apparatus according to claim 2, wherein said gas identifier identifies spectral information representing a spectral waveform which is most similar to a waveform of the spectrum representing the change in the color of said medium which is detected by said color change detector, and also representing a spectral waveform whose degree of conformity with the waveform of the spectrum representing the change in the color of said medium is greater than a predetermined value, from the spectral information stored in said database, and reads the gas identifying information related to the identified spectral information from said database.

4. The gas identifying apparatus according to claim 1, wherein said database stores said gas identifying information and an absorption line obtained from the color of the reagent which has chemically reacted with the gas identified by said gas identifying information, in relation to each other, and
    wherein said controller identifies an absorption line in accordance with the color detected by said detector, identifies an absorption line which is most similar to the identified absorption line from the absorption line stored in said database, and reads the gas identifying information related to the identified absorption line from said database.

5. The gas identifying apparatus according to claim 1, wherein said database stores color information depending on a detected result from said detector when said detector detects the color of said reagent which has chemically reacted with the gas identified by said gas identifying information.

6. The gas identifying apparatus according to claim 1, further comprising:
    a transmitter sending the gas identifying information that is read by said controller to an external information center.

7. The gas identifying apparatus according to claim 6, further comprising:
    a position output unit generating positional information representing a present position of said gas identifying apparatus,
    wherein said transmitter sends the positional information generated by said position output unit, together with said gas identifying information, to said external information center.

8. A gas handling assisting system comprising:
a gas identifying apparatus identifying a gas to be identified in accordance with a color of a reagent which has chemically reacted with the gas to be identified in a gas detecting device; and
an information center communicating with said gas identifying apparatus,
wherein said gas identifying apparatus comprises: said gas detecting device;
    a database storing, in advance, gas identifying information identifying a gas, and a color information as to a color of a reagent which has chemically reacted with the gas identified by said gas identifying information, in relation to each other;
    a detector detecting the color of the reagent which has chemically reacted with the gas to be identified in said gas detecting device;
    a controller identifying color information which is most similar to the color detected by said detector from the color information stored in said database, and reading the gas identifying information related to the identified color information from said database; and
    a transmitter sending the gas identifying information which is read by said controller to said information center,
wherein said information center comprises:
    a communication unit receiving information sent from said transmitter; and
    a display unit displaying the information received by said communication unit,
wherein said reacts with the gas to be identified when the reagent flows into a medium that is held in contact with the gas to be identified in said gas detecting device,
wherein said database stores, as said color information, color change information representing a change from a color of said medium before said reagent flows into said medium to a color of said medium after said reagent flows into said medium and chemically reacts with the gas,
wherein said detector detects the color of said medium before said reagent flows into said medium and the color of said medium after said reagent flows into said medium and chemically reacts with the gas,
wherein said controller comprises:

a color change detector detecting a change in the color of said medium in accordance with detected results from said detector; and a gas identifier identifying color change information, which is most similar to the change in the color of said medium which is detected by said color change detector, from the color change information stored in said database and reading the gas identifying information related to the identified color change information from said database, wherein said detector comprises:

a light-emitting element applying light to said medium;

an emitted-light guiding optical fiber guiding the light which is applied from said light-emitting element to said medium;

a photodetector; and a light guide guiding the light, which is applied from said light-emitting element and then reflected from said medium, to said photodetector, said light guide including:

an elliptical mirror; and a reflected-light guiding optical fiber disposed at a focal position of the elliptical mirror, and wherein said photodetector is disposed at another focal position of said elliptical mirror.

9. The gas handling assisting system according to claim 8, wherein said information center further comprises:

a handling information storage unit storing said gas identifying information and handling information representing how to handle the gas that is identified by the gas identifying information, in relation to each other; and a center controller reading handling information, which is related to the gas identifying information received by said communication unit, from said handling information storage unit, and displaying the read handling information on said display unit.

10. The gas handling assisting system according to claim 9, wherein said gas identifying apparatus further comprises:

a position output unit generating positional information representing a present position of said gas identifying apparatus, wherein said transmitter sends the positional information generated by said position output unit, together with said gas identifying information, to said external information center, wherein said information center further comprises:

a handling center storage unit storing handling center information representing a handling center and a territory covered by said handling center, in relation to each other, and wherein said center controller identifies a handling center whose territory includes the position represented by the positional information received by said communication unit, by referring to said handling center storage unit, and controls said communication unit to send said positional information and said read handling information to the identified handling center.

11. The gas identifying apparatus according to claim 1, wherein the database and the detector are located in substantially a same location.

12. The gas identifying apparatus according to claim 1, wherein the database is physically connected to the detector.

13. The gas identifying apparatus according to claim 8, wherein said reagent is stored in a breakable ampule such that, if the ampule is broken, then the reagent flows into the medium that is held in contact with the gas to be identified in said gas detecting device.

14. The gas identifying apparatus according to claim 1, further comprising the gas detecting device connected to the detector.

15. The gas identifying apparatus according to claim 1, further comprising a case including within the database, the detector and the controller.

16. The gas identifying apparatus according to claim 14, wherein the gas detecting device includes a plurality of different reagents and a plurality of separate detecting mediums on which colors of the plurality of different reagents are detected, respectively.

* * * * *